United States Patent [19]

Inns

[11] 3,972,602

[45] Aug. 3, 1976

[54] AUXILIARY LENS HOLDER DEVICE FOR USE WITH A KERATOMETER

[75] Inventor: H. D. E. Inns, Brantford, Canada

[73] Assignee: Precision-Cosmet Company, Inc., Minneapolis, Minn.

[22] Filed: Aug. 1, 1974

[21] Appl. No.: 493,827

[52] U.S. Cl. .................................. 351/6; 351/38
[51] Int. Cl.² .................................... A61B 3/10
[58] Field of Search ................... 351/6, 10, 38, 13

[56] References Cited
UNITED STATES PATENTS 3,416,855   12/1968   McClernon .......................... 351/6

FOREIGN PATENTS OR APPLICATIONS 597,062   1/1948   United Kingdom ..................... 351/6

OTHER PUBLICATIONS

L71400004 (Opt. J. Rev. Optom., vol. 107, No. 18, 9-15-70, p. 27).

Soper, et al., Archives of Opthalm., vol. 67, June 1962, pp. 753-760.

Primary Examiner—Paul A. Sacher
Attorney, Agent, or Firm—Williamson, Bains & Moore

[57] ABSTRACT

A lens holder device for mounting an auxiliary lens on a keratometer, comprises a generally circular disc which engages and mounts on the keratometer closely adjacent the front face thereof. The disc has a vertically oriented slot therein which is of a size to accommodate an auxiliary lens. The continuous U-shaped edge defined by the slot in the disc has a groove therein, which engages the edge of an auxiliary lens and positions the auxiliary lens in centered spaced relation with respect to the objective lens of the keratometer, thereby increasing the range of the keratometer.

3 Claims, 4 Drawing Figures

AUXILIARY LENS HOLDER DEVICE FOR USE WITH A KERATOMETER

SUMMARY OF THE INVENTION

This invention relates to an auxiliary lens holder device for a keratometer.

A keratometer instrument is one that is used to measure the corneal curvature of an eye and is used extensively in contact lens fitting. Keratometers have also been used to measure the anterior surface of soft corneal contact lens while in place on a patient. Certain commercial keratometers have an upper range limit, usually 52.00 diopters which is not high enough to measure the true corneal curvature of keratoconic patients, especially those patients suffering from a high degree of corneal astigmatism. Therefore, on some occasions, the practitioner must extrapolate in order to approximate the true corneal curvature or take some step to increase the actual range of the keratometer.

Auxiliary trial lenses have been used by some practitioners to extend the range of keratometers and this is probably the most popular and convenient method used to extend the range of the commercially available keratometers. However, one of the problems involved in the use of auxiliary trial lenses is the problem of exactly locating each successive trial lens at precisely the same location forwardly of the face plate of the keratometer. It is quite apparent that holding the trial lens by hand in front of the face plate of the instrument simply will not allow the practitioner to consistently position the trial lens in precisely one location. It has also been found that holding the trial lens closely adjacent the front of the instrument face often obstructs at least one of the mire signs.

It is therefore an object of this invention to provide an auxiliary lens holder device which may be readily mounted on a keratometer adjacent the front face thereof and which serves to provide a mounting for auxiliary trial lenses for extending the range of the keratometer.

More specifically, the lens holder device when mounted on a keratometer permits auxiliary trial lenses to be inserted in substantially precise centered spaced relation with respect to the objective lens of the keratometer. The lens holder device is also arranged and constructed so that no mire sign is obstructed by the holder device when the latter is mounted on the keratometer.

These and other objects and advantages of this invention will more fully appear from the following description made in connection with the accompanying drawings wherein like reference characters refer to the same or similar parts throughout the several views.

FIGURES OF THE DRAWING

DESCRIPTION OF THE PREFERRED EMBODIMENT OF THE INVENTION

Figure 1:
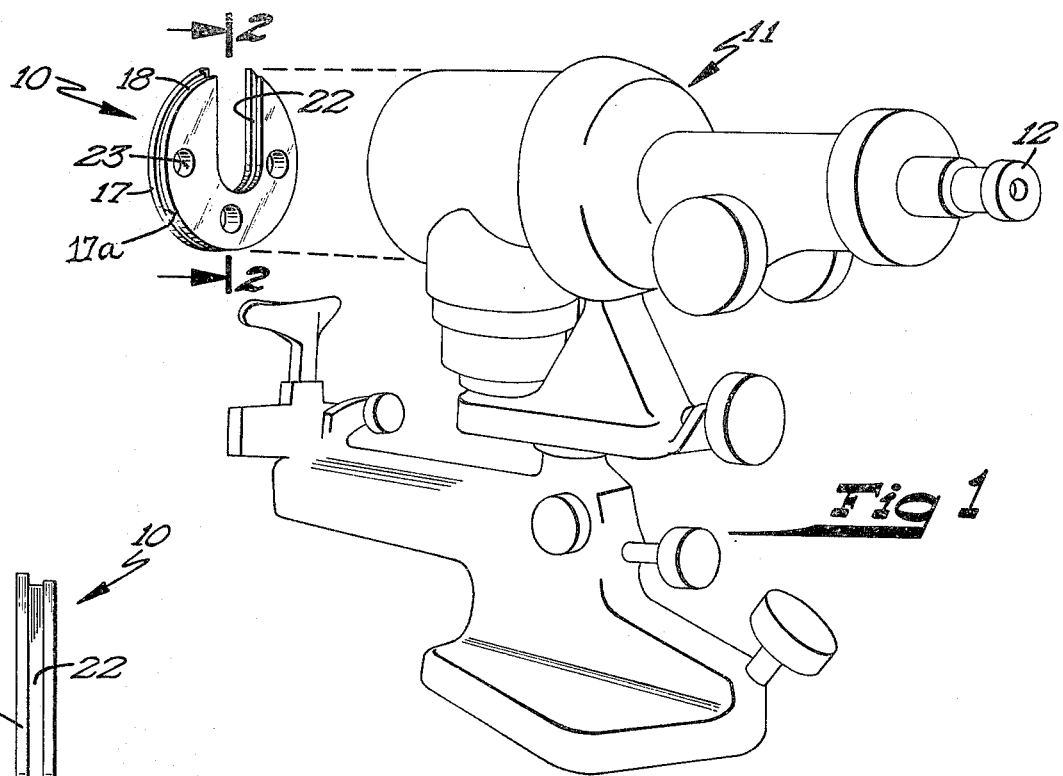
FIG. 1 is a rear perspective view of a keratometer and illustrating the novel auxiliary lens holder device in exploded relation thereto.
Figure 2:
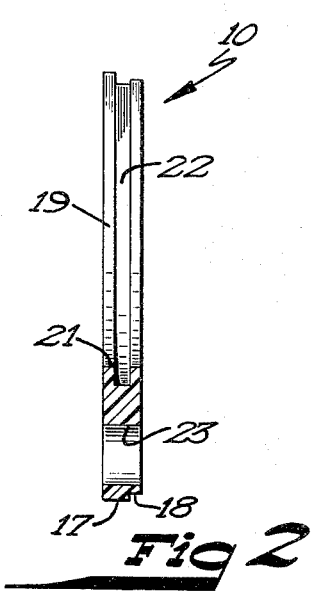
FIG. 2 is a cross-sectional view taken approximately along line 2—2 of FIG. 1.
Figure 3:
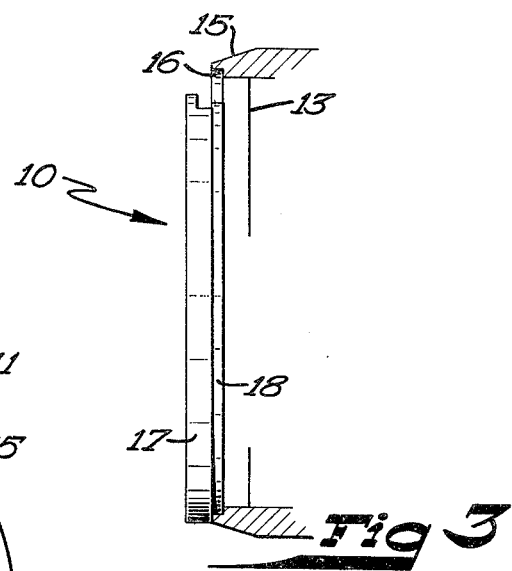
FIG. 3 is a side elevational view of the lens holder device illustrated in mounted relation with respect to the front end portion of the keratometer.
Figure 4:
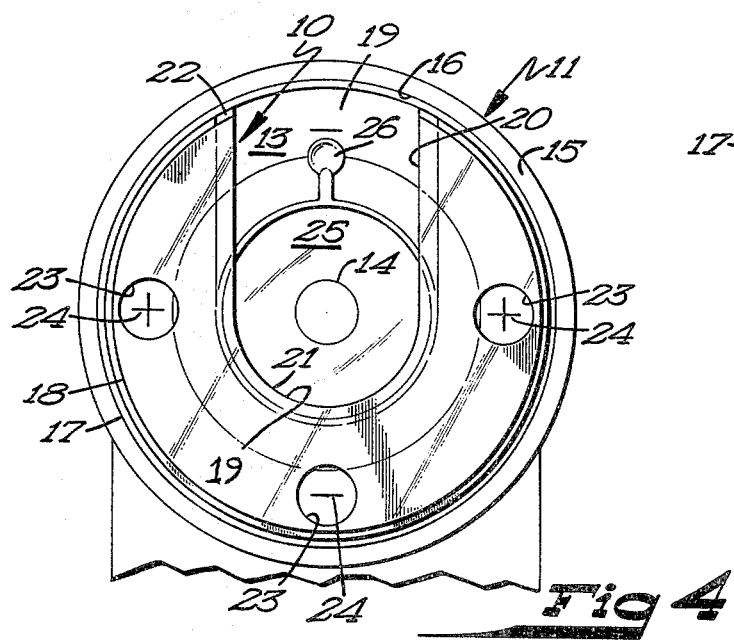
FIG. 4 is a front elevational view of the novel lens holder in mounted relation with respect to a keratometer and with a trial lens supported thereon.

Referring now to the drawings, and more specifically to FIG. 1, it will be seen that an auxiliary lens holder device, designated generally by the reference numeral 10, is illustrated in conjunction with a conventional keratometer 11. The keratometer 11 may be a commercially available unit such as the unit manufactured by Bausch & Lomb. The units are known in the trade as Bausch & Lomb Keratometers. Keratometers are used to measure curvatures of the corneas in dioptral values. The keratometer 11, which is of conventional construction, includes an eyepiece 12 at one end thereof and has a circular face plate 13 at the other end thereof. It will be noted that the circular face plate 13 has a substantially flat front surface and has an objective lens 14 mounted centrally therein. The keratometer 11 also has an annular lip 15 which projects axially forwardly from the face plate and presents a cylindrical inner surface 16.

On some occasions, the higher limit range of the keratometer, which is usually 52.00 diopters, is not high enough to measure the true corneal curvature, especially with keratoconic patients and those manifesting corneal astigmatism. The novel lens holder device 10 may be mounted on the keratometer, and provides a means for positioning successive auxiliary trail lenses in the same precise centered spaced relation with respect to the objective lens of the keratometer. In this respect, the auxiliary lens holder device 10, which may be formed of a suitable rigid non-metallic material such as plastic or the like, is of flat circular construction. In the embodiments shown, the auxiliary lens holder device is constructed of a transparent rigid plastic material. It will be noted that the lens holder device 10 has a circumferential edge surface 17 which is reduced at 18 to thereby define an annular shoulder 17a therebetween, the annular shoulder 17a separating the two circumferential surfaces. These two circumferential surfaces of the lens holder device permit the lens holder device to be mounted upon keratometers of different sizes.

The lens holder device 10 has a relatively large slot 19 therein which extends from the circumference of the lens holder device inward in a general radial direction beyond the center of the disc. It will be noted that the slot 19 defines a continuous U-shaped edge 19a, including substantially parallel side edge portions 20 and an arcuate edge portion 21. the continuous U-shaped edge 19a has an inwardly opening continuous groove 22 therein, the width dimension of the groove corresponding to the thickness dimension of an auxiliary trial lens. The auxiliary lens holder disc 10 also has three symmetrically spaced apart openings 23 therein, two of the openings being disposed in diametrically opposed relation with respect to each other.

The circular face plate 13 has four spaced apart mire signs 24 on the front surface adjacent the periphery thereof. It will be noted that there are two plus mire signs and two minus mire signs arranged in diametrically spaced apart pairs. When the lens holder device 10 is mounted in frictional engagement with the annular lip 15, the openings 23 in the lens holder device will be disposed in registering relation with three of the mire signs 24. The other mire sign 24 will be unobstructed as a result of the positioning of the slot 19.

In use, the lens holder device 10 will be applied so that either the larger circumferential surface 17 or the reduced circumferential surface 18 frictionally engages the inner surface 16 of the annular lip 15. when so applied to the keratometer, the lens holder device will engage the annular lip with a positive friction fit. The slot 19 will be oriented vertically, and the openings 23 will be disposed in registering relation with respect to the mire signs. The groove 22 in the continuous U-shaped edge of the slot 19 will be located forwardly of the annular lip 15.

With this arrangement, an auxiliary trial lens 25 may be readily mounted in centered spaced relation with respect to the keratometer objective lens by merely holding the trial lens by its tab 26 and urging the lens downwardly in the slot 19 until it is in seated relation in the arcuate edge portion 21. The circumferential edges of the auxiliary trial lens will be disposed in the inwardly opening groove 22, and when the trial lens 25 is seated in the arcuate edge portion 21 of the slot 19, the lens will be precisely centered with respect to the objective lens 14 of the keratometer 11. It will be seen that each successive trial lens mounted in the lens holder device will be precisely spaced from the keratometer objective lens and will be centered with respect thereto. It will also be noted that the openings 23 as well as the vertical orientation of the slot 19 permit the mire signs to be unobstructed at all times. thus the lens holder device may be retained in mounted relation on the keratometer since it in no way interferes with the operation even though no auxiliary trial lens is required.

From the foregoing description, it will be seen that I have provided a novel auxiliary lens holder device which may be readily mounted on the front end portion of a keratometer and which serves to support and precisely position auxiliary trial lenses for use in extending the range of the keratometer.

Thus, it will be seen that I have provided an auxiliary lens holder device which is not only of simple and inexpensive construction, but one which functions in a more efficient manner than any heretofore known comparable device.

What is claimed is:

1. A lens holder device for a keratometer including an eyepiece, a substantially circular front face plate having a centrally located objective lens therein, an annular lip projecting axially forwardly from the face pate, diametrically opposed pairs of mire signs on the face plate, said lens holder device comprising:

a generally flat circular disc.

a slot in the disc extending inwardly, in a general radial direction from the circumferential edge thereof beyond the center of the disc, said slot defining a U-shaped edge including side edge portions and an arcuate inner portion continuous with said side edge portions, said U-shaped edge having a continuous inwardly opening groove therein, said slot being of the size to accommodate an auxiliary optical trial lens therein with the edge of the trial lens positioned in the groove, said disc being of the size to permit the circumferential edge thereof to frictionally engage the inner surface of the forwardly projecting annular lip of the keratometer to mount the disc on the latter in forwardly spaced relation with respect to the objective lens of the keratometer, the slot in the disc being oriented in the vertical direction when the disc is mounted on the keratometer, with the groove in the disc being positioned forwardly of the annular lip, whereby an auxiliary trial lens seated in the arcuate edge portion of the slot will be centered with respect to the keratometer objective lens.

2. The lens holder device as defined in claim 1 and a plurality of openings in said disc, each being of a size slightly larger than a mire sign and each being disposed in registering relation with a mire sign on the face plate of the keratometer when the disc is mounted on the latter.

3. a lens holder device as defined in claim 1 wherein the circumferential edge of the disc includes a reduced portion to permit mounting of the disc on keratometers of a different size.

* * * * *